United States Patent [19]
Leinfelder et al.

[11] Patent Number: 5,257,932
[45] Date of Patent: Nov. 2, 1993

[54] DENTAL ARTICULATOR WITH CONDYLE STRAIN INDICATION

[76] Inventors: Marcus J. Leinfelder, 3814 Holly Pl.; Robert J. Harter, 4233 Cliffside Dr., both of La Crosse, Wis. 54601

[21] Appl. No.: 775,151

[22] Filed: Oct. 9, 1991

[51] Int. Cl.⁵ ............................................. A61C 11/00
[52] U.S. Cl. ........................................ 433/56; 433/55
[58] Field of Search ................ 433/55, 56, 57, 61, 433/65, 68, 69

[56] References Cited

U.S. PATENT DOCUMENTS

| | | | |
|---|---|---|---|
| Re. 31,716 | 10/1984 | Lee | 433/56 |
| 2,275,726 | 3/1942 | Burns et al. | 433/65 X |
| 2,701,915 | 2/1955 | Page . | |
| 2,713,721 | 7/1955 | Page . | |
| 2,763,061 | 9/1956 | Bergstrom | 433/57 |
| 2,768,442 | 10/1956 | DeFurio | 433/56 |
| 2,968,868 | 1/1961 | Page . | |
| 2,982,025 | 5/1961 | Page . | |
| 3,035,348 | 5/1962 | Page . | |
| 3,206,852 | 9/1965 | Swanson . | |
| 3,343,264 | 9/1967 | Guicket | 433/56 |
| 3,350,782 | 7/1967 | Guicket | 433/55 |
| 3,409,986 | 11/1968 | Freeman . | |
| 3,478,431 | 11/1969 | DePietro . | |
| 4,155,163 | 5/1979 | Schwartz | 433/65 X |
| 4,439,150 | 3/1984 | Edwardson | 433/56 |
| 4,443,191 | 4/1984 | Gutierrez | 433/56 |
| 4,459,108 | 7/1984 | Mack | 433/55 |
| 4,468,198 | 8/1984 | Kataoka et al. | 433/65 X |
| 4,668,189 | 5/1987 | Levandoski . | |
| 4,981,437 | 1/1991 | Wilcox | 433/55 |

OTHER PUBLICATIONS

Hanau Instruction Manual; Author Unknown; pp. 1-28; Date of Publication Unknown; Buffalo, New York.
Denar Instruction Manual; Author Unknown; pp. 1-14; Dated 1989; Anaheim, California.

*Primary Examiner*—Gene Mancene
*Assistant Examiner*—Nicholas D. Lucchesi

[57] ABSTRACT

A jaw model articulator clearly identifies condyle joint strain as well as fully emulates a patient's straight bite and cross bite. The spatial relationship of the upper and lower jaws with respect to the condyle joints and to each other is accurately determined by just two wax bite impressions taken of the patient. No extraneous mechanical hardware needs to be attached to the patient's head. The two wax impressions are sequentially inserted between the upper and lower jaw models. The resulting change in the models relative positions are measured and the values inputted to a desk top personal computer. The computer calculates the precise location of the rotational axis defined by the condyle joints, and the articulator is set up accordingly.

18 Claims, 5 Drawing Sheets

DENTAL ARTICULATOR WITH CONDYLE STRAIN INDICATION

BACKGROUND OF THE INVENTION

1. Field of the Invention

The subject invention generally pertains to a jaw model articulator, and more specifically to one that emulates a straight bite and cross bite, and further identifies condyle joint strain.

2. Description of Related Art

Dental articulators control the relative motion of upper and lower jaw models to emulate the relationship between the actual mandible and maxilla that the models represent. To properly set up an articulator, various means have been devised to locate the actual position of the condyle joints. This information is then used in determining the rotational axis about which the mandible pivots (until the teeth come together). Existing articulators and associated apparatus are disclosed in U.S. Pat. Nos. 1,161,504; 2,701,915; 2,713,721; 2,968,868; 2,982,025; 3,035,348; 3,206,852; 3,409,986; 3,478,431; and 4,668,189 all of which are specifically incorporated by reference herein.

Current articulators fail miserably in accurately locating the condyles. Typical devices use sophisticated brackets with adjustable pointers that clamp to a patient's lower jaw. The action of the pointer as the patient's mouth opens and closes is observed and used as a basis for locating the condyles. The typical articulator is then set up accordingly. Wax bite impressions used to confirm the setting often blatantly demonstrate the inadequacy of such devices.

Out of frustration other articulators have emerged that operate based on the over-simplified assumption that all condyles are located the same specific distance from the ear canal. Such an assumption makes for a very "user friendly" articulator. Accordingly, some articulators use "locators" that are simply inserted in the patient's ears. Although easy to use, they are not accurate.

A further shortcoming of existing articulators is that they disregard the disruptive effect that intermeshing teeth can have on an otherwise natural path of the lower jaw. Clenching teeth can strain one or both condyles. Current articulators fail to identify such strain which further frustrates dentists as their patients complain of joint pain or a hideous "popping" or "clicking" sound while chewing.

SUMMARY OF THE INVENTION

To avoid the limitations and problems with present articulators, it is an object of the invention to control the movement of two jaw models to approximate the corresponding patient's actual jaw movements in both a straight bite and cross bite.

Another object of the invention is to demonstrate any condyle joint strain that may be occurring as the patient bites.

Yet another object of the invention is to emulate the chewing motion of a patient's jaws by controlling the translational movement of a jaw model along a line about which the jaw model revolves.

A further object is to eliminate the need for mounting extraneous hardware on a patient's head by determining the spatial relationship of two jaw models and their rotational axis based on just two wax bite impressions.

A still further object is to use a personal computer to calculate the position of a rotational axis about which a jaw model revolves with respect to another jaw model.

The subject invention provides a revolutionary dental articulator that is not only extremely accurate, but it is also the only one that identifies condyle joint strain. The subject invention is unquestionably the state-of-the-art in dental articulators.

A feature of the invention is a three-position coupling that controls the movement of a jaw model about a shaft such that in one position allows only rotational movement, in a second position allows rotational and axial movement, and a third position allows rotational, axial, and radial movement.

These and other objects of the invention are provided by a novel articulator on which two jaw models can be mounted. The articulator includes a shaft that is mounted along a rotational axis about which one model revolves with respect to the other. The location of the shaft is determined based on the change in position of one of the jaw models upon sequentially inserting two wax bite impressions between the jaw models.

DESCRIPTION OF THE PREFERRED EMBODIMENT

Structure

Figure 1:
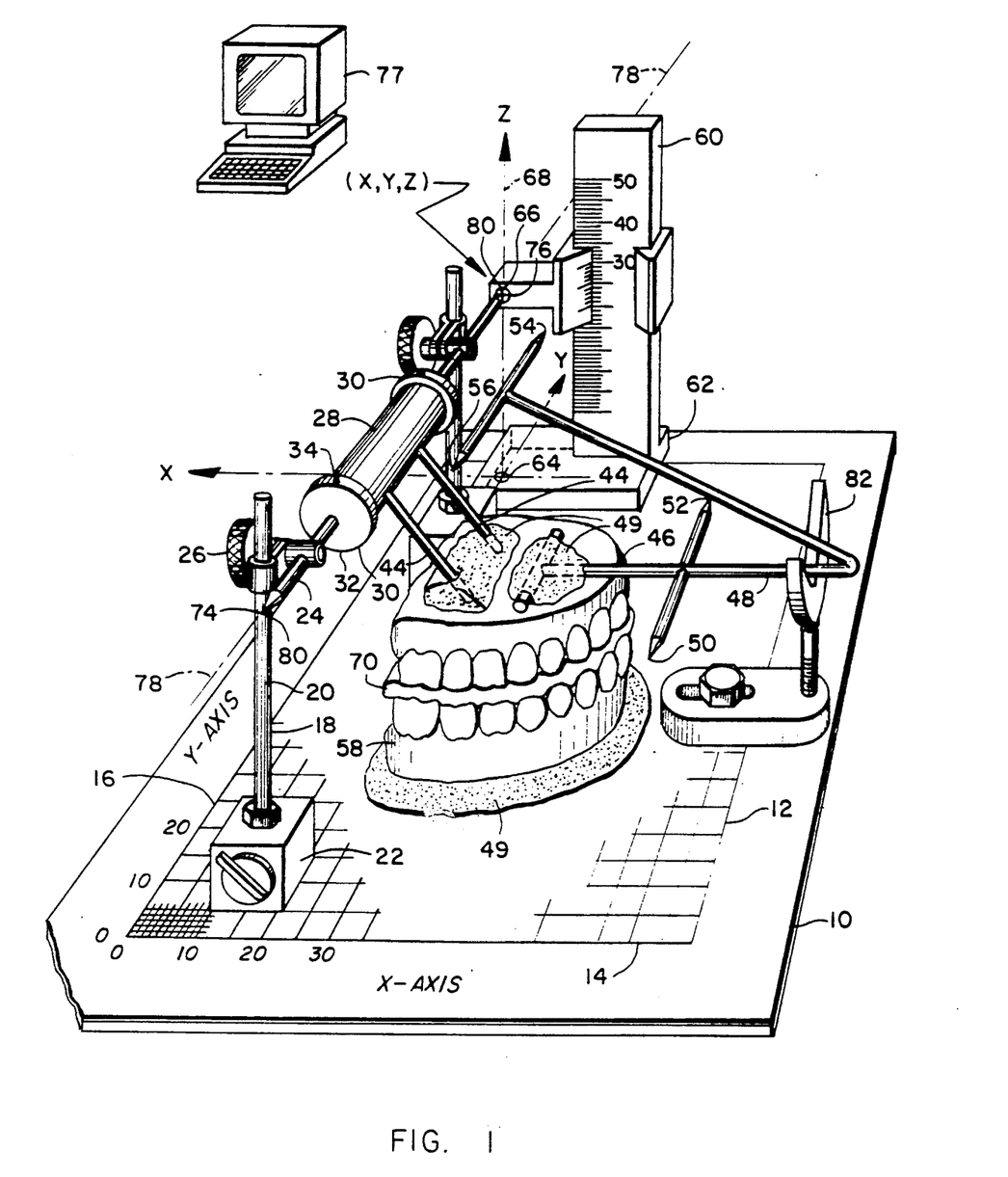
FIG. 1 shows the rule identifying where one end of the shaft should be located. The thinner wax bite is in place to put the upper jaw model at a first position.

Referring to FIG. 1, the subject invention includes a flat steel base 10 having a rectangular grid 12 printed on its surface. Grid 12 is 180 mm by 250 mm (45,000 squares) and is graduated in millimeters. A 180 mm edge 14 of grid 12 defines an X-axis and an adjacent perpendicular 250 mm edge 16 defines the Y-axis. Base 10 provides a convenient datum from which measurements can be taken.

An adjustable shaft support 18 is attached to base 10. In one embodiment of the invention, support 18 includes two vertical ⅜" diameter rods 20 threaded to a magnetic base 22. Another ⅜" diameter shaft 24 is supported generally horizontally across rods 20. Shaft 24 is clamped firmly to rods 20 by way of two conventional shaft clamps 26.

Figures 4, 5, 6:
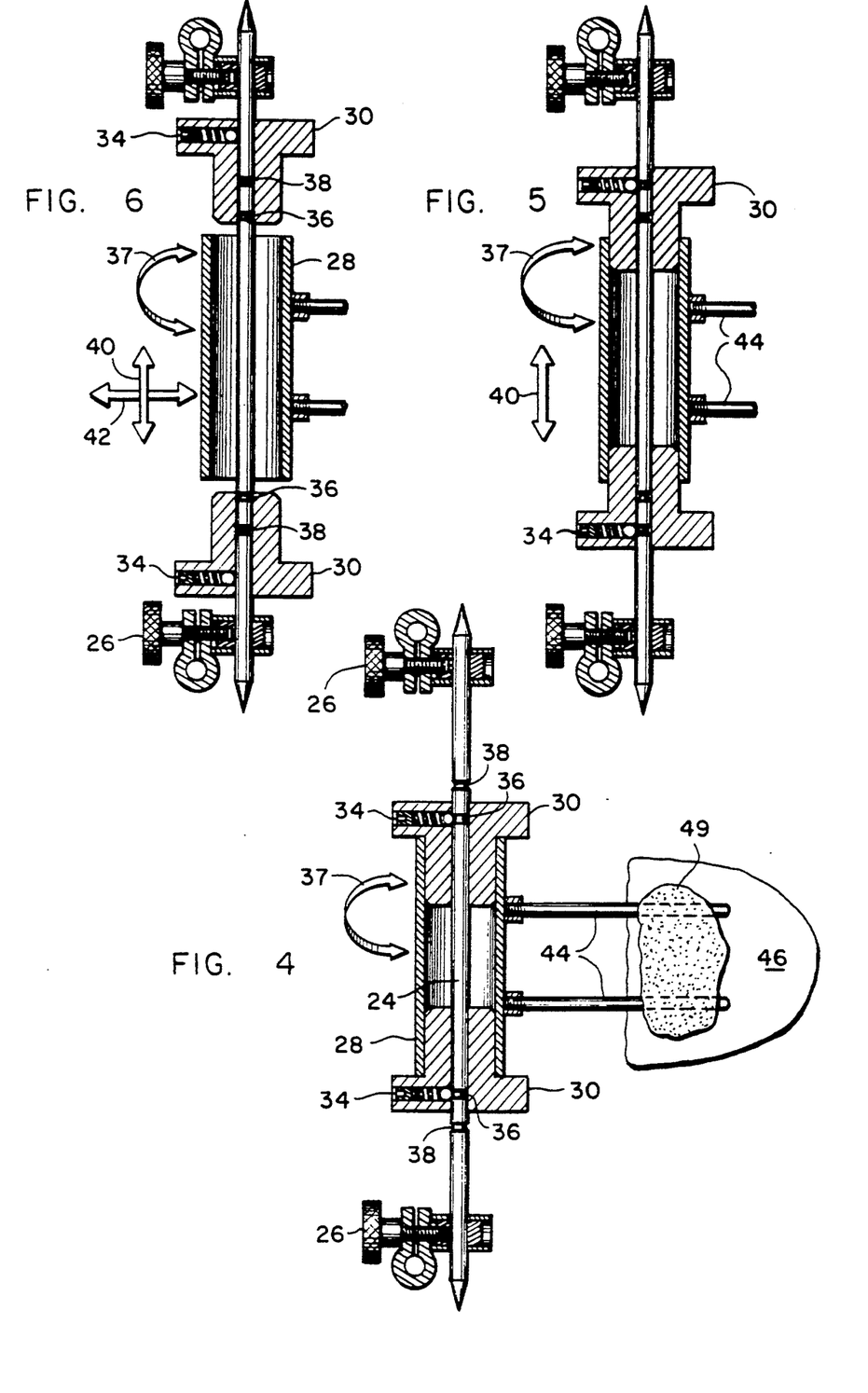
FIG. 4 is a sectional view with the coupling in a position to allow only rotational movement of the upper jaw model.
FIG. 5 is a sectional view with the coupling in a position to allow rotational and axial movement of the upper jaw model.
FIG. 6 is a sectional view with the coupling in a position to allow rotational, axial, and radial movement of the upper jaw. Any misalignment between the bushings and the cylinder indicates condyle joint strain.

With further reference to FIGS. 4-6, a cylinder 28 having a ⅞" inside diameter is situated around shaft 24. Two flanged bushings 30 having an inside diameter slightly over ⅞" and a minor outside diameter slightly under ⅞" provides a disengagable coupling that rotatably centers cylinder 28 radially around shaft 24. Spring loaded detent ball plungers 34 in each bushing 30 in conjunction with an inner pair of circumferential grooves 36 around shaft 24 serve to axially position bushings 30 on shaft 24. When ball plungers 34 engage the inner set of grooves 36, cylinder 28 is approximately centered axially on shaft 24 and can rotate 37 about it. When ball plungers 34 engage an outer set of grooves 38 spaced further apart than the first, bushings 30 keep cylinder 28 radially centered about shaft 24 but allow cylinder 28 to slide in an axial direction 40 back and forth parallel to shaft 24. When bushings 30 are separated even further, cylinder 28 becomes free to move radially 42 within the confines of the clearance between the ⅞" diameter of shaft 24 and the ⅞" diameter of cylinder 28.

Cylinder 28 has two radially protruding arms 44 that are adapted to be cemented to an upper jaw model 46.

A pointer 48 is also adapted for cementing to upper jaw model 46. Pointer 48 includes four reference points 50, 52, 54 and 56 from which to measure a spatial change in position of upper jaw model 46 with respect to base 10, a lower jaw model 58, or some other predetermined datum. The distance between points 50 and 52 as well as the distance between points 54 and 56 is approximately 4.5 inches.

A rule 60 graduated in millimeters similar to the graduations of grid 12 is for measuring the position of reference points 50, 52, 54 and 56. In one embodiment of the invention, rule 60 is a vernier height gage. Height gage 60 includes a transparent base 62 marked with a lower set of cross-hairs 64 and having a vertically movable upper set of cross-hairs 66. Cross-hairs 64 and 66 are aligned directly above each other. An imaginary line 68 passing through both of their center points is referred to as the Z-axis 68. When rule base 62 is placed atop base 10, Z-axis 68 is substantially perpendicular to the X and Y axes.

Setup

One step is to make models 46 and 58 of a patient's upper and lower jaws. Methods for preparing such models are well known by those skilled in the art.

In addition, at least two wax bite impressions 70 and 72 are taken of the patient's mouth. Again, this is common practice with those skilled in the art. One thin impression 70 (approximately 3 mm thick) is taken where the patient bites squarely and naturally into the wax but avoids engaging the teeth of the upper jaw with those of the lower jaw. The second bite impression 72 (see FIG. 2) is similar but approximately 10 mm thicker.

Figure 2:
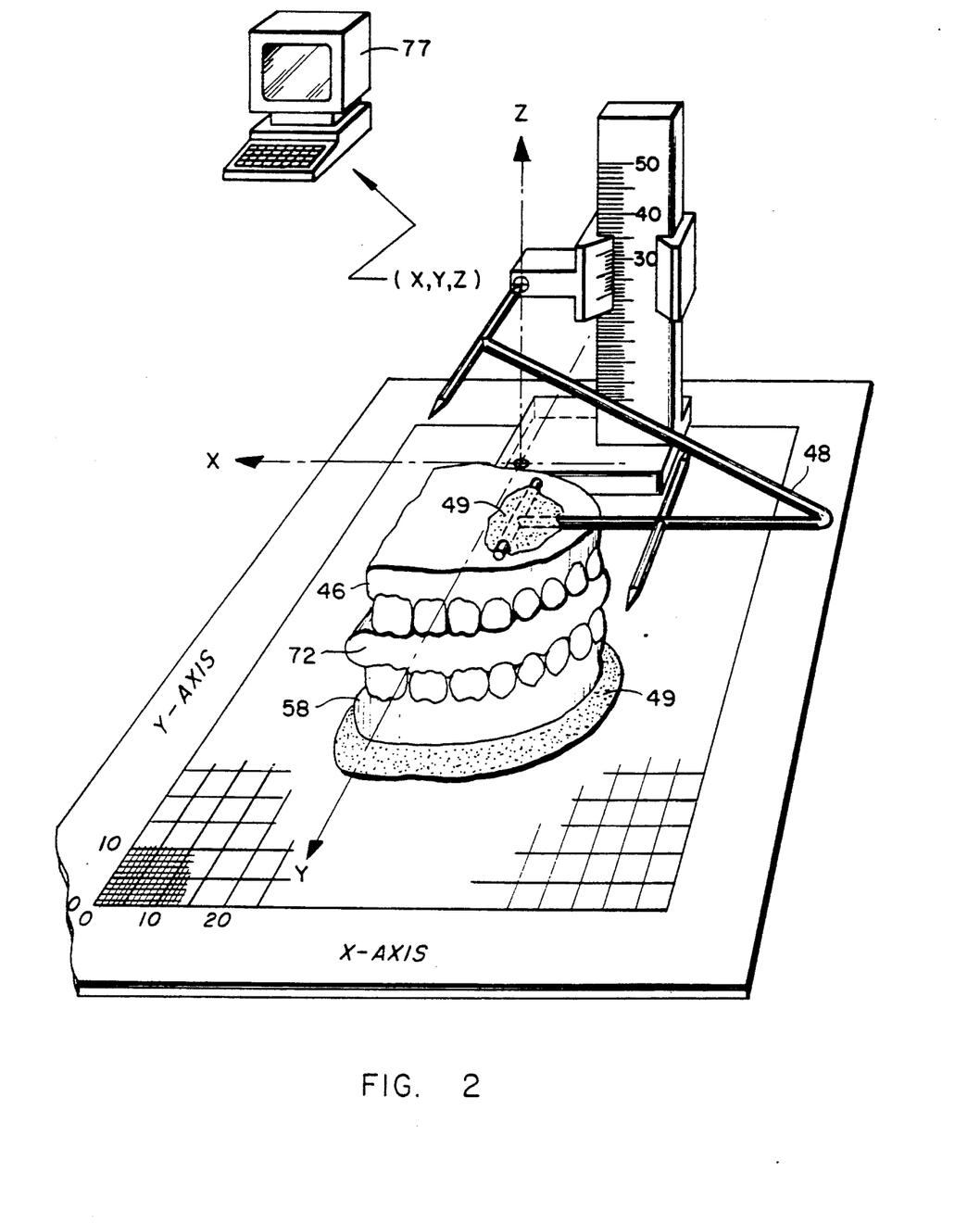
FIG. 2 shows the rule measuring the location of one point of the pointer. The thicker wax bite is in place to put the upper jaw model at a second position.

A first jaw model, e.g., upper jaw 46, is cemented by conventional means to pointer 48, as shown in FIG. 2. A second jaw model, e.g., lower jaw 58, is attached with cement 49 (or in some other way attached) to base 10 at a convenient place.

With lower jaw model 58 fixed with respect to base 10, upper jaw model 46 with pointer 48 is placed at a first position (FIG. 1) on top of lower jaw model 58 with thinnest wax impression 70 sandwiched therebetween. Wax impression 70 aligns jaw models 46 and 58 with respect to each other.

A position measurement of each of the four reference points 50, 52, 54 and 56 is taken. Transparent base 62 of height gage 60 is slid horizontally over base 10, and the upper set of cross-hairs 66 are slid vertically until upper cross-hairs 66 meet one of reference points 50, 52, 54 and 56. At that position, rule 60 indicates the XYZ spatial position coordinate of that reference point. Lower cross-hairs 64 superimposed on grid 12 of base 10 indicate the X and Y components, while upper cross-hairs 66 with reference to the graduations on rule 60 indicate the Z component. After noting the X, Y, and Z coordinate measurements, position measurements of the remaining three reference points are taken.

The thinnest wax impression 70 is replaced by thicker wax impression 72 to move upper jaw model 46 to a second position (as shown in FIG. 2), emulating opening of the patient's mouth. Position measurements are again taken of the four reference points 50, 52, 54 and 56, just as was done when the thinnest wax impression 70 was in place.

The eight position measurements each having an X, Y, and Z component are used to calculate two XYZ output coordinate points 74 and 76 defining a rotational axis 78 about which points 50, 52, 54 and 56 effectively revolve as upper jaw model 46 moves from the first to second position. The means for calculating the two output coordinate points 74 and 76 involve basic algebra and geometry, and can be calculated by a variety of means ranging from long hand to a computer 77. In one embodiment of the invention, the FORTRAN program shown below provides one means for calculating output points 74 and 76.

```
      DIMENSION DD(24),OF(6)

REAL*4 IZ,IX,JZ,JX,KX,KZ,KY,LX,LZ,LY,MX,MY,MZ,LENP,LENR
      REAL*4 LX2,LY2,LZ2,KX2,KY2,KZ2
C
      CHARACTER*2 STR(8)
C
      DATA STR/
     1   'A1','A2','B1','B2','C1','C2','D1','D2'/
C
C
      WRITE(*,1010)
   10 CALL TE(DD)
C
      DO 30 J=1,4
```

```
      DO 20 K=1,3
      I=6*(J-1)+K
      DD(I)=DD(I)+0.001
20    CONTINUE
30    CONTINUE
C
      GZ=0.5*(DD(3)+DD(6))
      GX=0.5*(DD(1)+DD(4))
      HZ=0.5*(DD(9)+DD(12))
      HX=0.5*(DD(7)+DD(10))
      IZ=0.5*(DD(15)+DD(18))
      IX=0.5*(DD(13)+DD(16))
      JZ=0.5*(DD(21)+DD(24))
      JX=0.5*(DD(19)+DD(22))
C
      A=(DD(1)-DD(4))/(DD(3)-DD(6))
      B=(DD(7)-DD(10))/(DD(9)-DD(12))
      C=(DD(13)-DD(16))/(DD(15)-DD(18))
      D=(DD(19)-DD(22))/(DD(21)-DD(24))
C
      KX=(GZ+A*GX-HZ-B*HX)/(A-B)
      KZ=-B*KX+HZ+B*HX
      KY=0.25*(DD(2)+DD(5)+DD(8)+DD(11))
      LX=(IZ+C*IX-JZ-D*JX)/(C-D)
      LZ=-D*LX+JZ+D*JX
      LY=0.25*(DD(14)+DD(17)+DD(20)+DD(23))
C
      MX=0.5*(KX+LX)
      MY=0.5*(KY+LY)
      MZ=0.5*(KZ+LZ)
      LENP=SQRT((LX-KX)**2+(LY-KY)**2+(LZ-KZ)**2)
      LENR=242.
      PCT=LENR/LENP-1.
C
      LX2=LX+PCT*(LX-MX)
      LY2=LY+PCT*(LY-MY)
      LZ2=LZ+PCT*(LZ-MZ)
      KX2=KX-PCT*(MX-KX)
      KY2=KY-PCT*(MY-KY)
      KZ2=KZ-PCT*(MZ-KZ)
      OP(2)=0.5*(250.-(LY2-KY2))
      OP(5)=250.-OP(2)
      MX=(LY2-KY2)/(LX2-KX2)
      BX=LY2-MX*LX2
      OP(1)=(OP(2)-BX)/MX
      OP(4)=(OP(5)-BX)/MX
      MZ=(LZ2-KZ2)/(LY2-KY2)
      BZ=LZ2-MZ*LY2
      OP(3)=MZ*OP(2)+BZ
      OP(6)=MZ*OP(5)+BZ
C
      DO 50 J=1,4
      DO 40 K=1,3
      I=6*(J-1)+K
      DD(I)=DD(I)-0.001
40    CONTINUE
50    CONTINUE
      WRITE(*,10020)
      WRITE(*,10030)
      WRITE(*,10050)
      WRITE(*,10040)
C
      DO 70 J=1,4
      WRITE(*,*)
      DO 60 I=1,2
```

```
      K=3*(2*(J-1)+I-1)
      M=2*(J-1)+I
      WRITE(*,10060) STR(M),(DD(L),L=K+1,K+3)
   60 CONTINUE
   70 CONTINUE
      WRITE(*,10080)
      WRITE(*,10070)
      WRITE(*,10060) 'E ',(OP(I),I=1,3),'F ',(OP(I),I=4,6)
      WRITE(*,10090)
      GO TO 10
10010 FORMAT(//////' You can now enter your measurements in any'
     1 /' order.  For example:'//,
     2 '    > C1Y 46.7 (Enter or Return)'/,
     3 '    > A2X 50'/,
     4 '    > D2X 21.3'/,
     5 '    > C1Y 46.6 (To change original 46.7 reading to 46.6)'///,
     6 ' Or you can enter any of the following commands:'//,
     7 ' "DISPLAY"  displays your measurements in a chart'/,
     8 ' "SAVE"   stores your measurements'/,
     9 ' "GET"    retrieves a chart you saved earlier'/,
     1 ' "RUN"    calculates the rotational point "E" and "F"'/,
     2 ' "CLEAR"  deletes all data in current chart'/,
     3 ' "EXIT"   exits from the program'/,
     4 ' "WALK"   provides another way to enter measurements'/)
10020 FORMAT(//)
10030 FORMAT(22X'ARTHROGRAPH',/
     1  13X'Trademark of Mark Leinfelder'/)
10040 FORMAT('                                                          ')
10050 FORMAT('       POINTS       X           Y           Z')
10060 FORMAT(7X,A2,F11.1,2F13.1)
10070 FORMAT('                                                          ')
10080 FORMAT(/'      SETTINGS      X           Y           Z')
10090 FORMAT(/10X,'(Copyright 1991 by Mark Leinfelder)')
      END SUBROUTINE TE(DD)
C
C ----- SUBROUTINE TO ACCEPT THE DATA INPUT FROM THE TERMINAL.
C       ALSO DOES OTHER GOOD THINGS.
C
      LOGICAL YES
C
      DIMENSION DD(1)
      DIMENSION B(20),C(10)
C
      CHARACTER*1 BELL
      CHARACTER*127 STRING
      CHARACTER*75 STR
      CHARACTER*5 A
      CHARACTER*40 DFIN
C
      EQUIVALENCE (STR,HLP)
C
      CHARACTER*5 VOC( 31)
      DATA VOC/
     1 'A1X  ','A1Y  ','A1Z  ','A2X  ','A2Y  ','A2Z  ','B1X  ','B1Y  ',
     2 'B1Z  ','B2X  ','B2Y  ','B2Z  ','C1X  ','C1Y  ','C1Z  ','C2X  ',
     3 'C2Y  ','C2Z  ','D1X  ','D1Y  ','D1Z  ','D2X  ','D2Y  ','D2Z  ',
     4 'RUN  ','GET  ','SAVE ','EXIT ','DISPL','CLEAR','WALK '/
      DATA NVOC/ 31/
```

```
C
      DATA NOW/0/
      IF(NOW.EQ.0)THEN
          DFIN='BYTE.DAT'
          IIN=12
          NOW=1
          BELL=CHAR(7)
          NVOC1=NVOC-7
      ENDIF
   10 WRITE(*,10070)
      CALL TERIF(A,B,C)
      IF(A.LE.' ')GO TO 10
      CALL CTUC(5,A)
      J=0
C
      DO 20 I=1,NVOC
      IF(A.EQ.VOC(I))THEN
          IF(I.GT.NVOC1)GO TO 30
          J=1
          DD(I)=C(1)
      ENDIF
   20 CONTINUE
      IF(J.EQ.0)THEN
          WRITE(*,10080) BELL
      ENDIF
      GO TO 10
   30 CONTINUE
      GO TO(40,50,100,120,130,150,170),I-NVOC1
C
C ----- RUN.
C
   40 CONTINUE
      RETURN
C
C ----- GET.
C
   50 CONTINUE
      STRING=' '
      WRITE(STRING,10090) (B(I),I=1,10)
      IF(STRING(1:40).EQ.' ')STRING(1:40)=DFIN
      INQUIRE(FILE=STRING,EXIST=YES)
      IF(YES)THEN
          OPEN(IIN,FILE=STRING,STATUS='OLD')
          DFIN=STRING(1:40)
      ELSE
          WRITE(*,10020)
          GO TO 10
      ENDIF
C
      DO 60 J=1,NVOC1
      DD(J)=0.
   60 CONTINUE
C
      DO 80 J=1,NVOC1
      READ(IIN,10050,END=90) STRING
C
      DO 70 K=1,NVOC1
      IF(STRING(1:5).EQ.VOC(K))THEN
          READ(STRING,10100) X,DD(K)
          GO TO 80
      ENDIF
   70 CONTINUE
   80 CONTINUE
   90 CLOSE(IIN)
      GO TO 10
```

```
C
C ----- SAVE.
C
  100 CONTINUE
      STRING=' '
      WRITE(STRING,10090) (B(I),I=1,10)
      IF(STRING(1:40).EQ.' ')STRING(1:40)=DFIN
      DFIN=STRING(1:40)
      OPEN(IIN,FILE=STRING,STATUS='UNKNOWN')
C
      DO 110 J=1,NVOC1
      IF(DD(J).NE.0.)WRITE(IIN,10100) VOC(J),DD(J)
  110 CONTINUE
      CLOSE(IIN)
      GO TO 10
C
C ----- EXIT.
C
  120 CONTINUE
      STOP
C
C ----- DATA.
C
  130 CONTINUE
      K=0
      STRING=' '
C
      DO 140 I=1,NVOC1
      K=K+1
      J=20*(K-1)+8
      STRING(J+1:J+5)=VOC(I)
      STRING(J+6:J+6)=':'
      WRITE(STRING(J+7:),10010) DD(I)
      IF(K.GE.3)THEN
          IF(MOD(I,6).EQ.3) WRITE(*,10010)
          WRITE(*,10040) STRING(1:79)
          K=0
          STRING=' '
      ENDIF
  140 CONTINUE
      IF(K.GT.0)THEN
          WRITE(*,10040) STRING(1:79)
      ENDIF
      GO TO 10
C
C ----- CLEAR.
C
  150 DO 160 I=1,NVOC1
      DD(I)=0.
  160 CONTINUE
      GO TO 10
C
C ----- WALK.
C
  170 WRITE(*,10060)
C
      DO 180 I=1,NVOC1
      WRITE(*,10030) VOC(I)
      READ(*,10110) DD(I)
  180 CONTINUE
      GO TO 10
10010 FORMAT(F7.1)
10020 FORMAT(/' File not found.')
10030 FORMAT('  > ',A5,1X,$)
```

```
10040 FORMAT(1X,A79)
10050 FORMAT(A127)
10060 FORMAT(/' Type in the value of the variable as they appear on',
     1       ' the screen.',/' If you want to omit the command just hit',
     2       ' RETURN.'/)
10070 FORMAT('  > ',$)
10080 FORMAT(1X,A1,' Data not accepted!')
10090 FORMAT(20A4)
10100 FORMAT(A5,1P,4E15.7)
10110 FORMAT(BN,4F16.0)
      END SUBROUTINE TERIP(A,B,C)
      CHARACTER*5 A
      CHARACTER STRING*80,D(80)*1
      DIMENSION C(10),B(15)
      READ(*,10010) D
C
      DO 10 I=1,5
      I1=I
      IF(D(I).EQ.' ')GO TO 20
   10 CONTINUE
   20 WRITE(STRING,10010) (D(I),I=1,I1)
      READ(STRING,10020) A
      I1=I1+1
C
      DO 30 I=I1,80
      I2=I
      IF(D(I).NE.' ')GO TO 40
   30 CONTINUE
   40 CONTINUE
      WRITE(STRING,10010) (D(I),I=I2,80)
      READ(STRING,10030) B
C
      DO 100 N=1,10
      C(N)=0.
      I1=I2
      IF(I1.GE.80)GO TO 100
C
      DO 50 I=I1,80
      I2=I
      IF(D(I).NE.' ')GO TO 60
   50 CONTINUE
   60 I1=I2
      IF(I1.GE.80)GO TO 100
C
      DO 70 I=I1,80
      I2=I
      IF(D(I).EQ.' ')GO TO 80
   70 CONTINUE
   80 D(I2)=','
      WRITE(STRING,10010) (D(I),I=I1,I2)
      READ(STRING,10040,ERR=90) C(N)
   90 I2=I2+1
  100 CONTINUE
      RETURN
10010 FORMAT(80A1)
10020 FORMAT(15A5)
10030 FORMAT(20A4)
10040 FORMAT(F12.0)
      END
```

```
SUBROUTINE CTUC(N,STRING)
CHARACTER*1 STRING(1)
C
    DO 10 I=1,N
    IF(STRING(I).GE.'a' .AND. STRING(I).LE.'z')THEN
        STRING(I)=CHAR(ICHAR(STRING(I))-32)
    ENDIF
10  CONTINUE
    RETURN
    END
```

With the thinnest wax impression 70 in place, input variables DD1, DD2, and DD3 correspond to the X, Y, and Z position measurements of point 56 respectively; DD7, DD8, and DD9 correspond to X, Y, and Z of point 50; DD13, DD14, and DD15 correspond to X, Y, and Z of point 54; and DD19, DD20, and DD21 correspond to X, Y, and Z of point 52. With the thicker wax impression in place, input variables DD4, DD5, and DD6 correspond to the X, Y, and Z position measurements of point 56 respectively; DD10, DD11, and DD12 correspond to X, Y, Z of point 50; DD16, DD17, and DD18 correspond to X, Y, Z of point 54; and DD22, DD23, and DD24 correspond to X, Y, Z of point 52. "LENR" represents the length of shaft 24. Calculated output variables OP1, OP2, and OP3 respectively correspond to the X, Y, and Z components of point 74 and OP4, OP5 and OP6 represent the X, Y, and Z of point 76.

Shaft 24 and adjustable shaft support 18 are locked to base 10 with the longitudinal center line of shaft 24 in collinear alignment with rotational axis 78. In one embodiment of the invention, this is done by marking a center line point 80 at each end of shaft 24. Rule 60 is positioned so that cross-hairs 64 and 66 correspond to one calculated output coordinate 74. Shaft 24, supported by adjustable shaft support 18, is positioned to align one of its center line points 80 to the upper set of cross-hairs 66. Likewise, the other center line point 80 is set at the other calculated output coordinate 76.

The thicker wax impression 72 is removed, and the thinner one 70 is once again placed between jaw models 46 and 58. Bushings 30 are placed at the inner pair of shaft grooves 36 to axially and radially align cylinder 28 to shaft 24.

Cylinder 28 is coupled to upper jaw model 46 by cementing arms 44 to upper jaw model 46.

Operation

Figure 3:
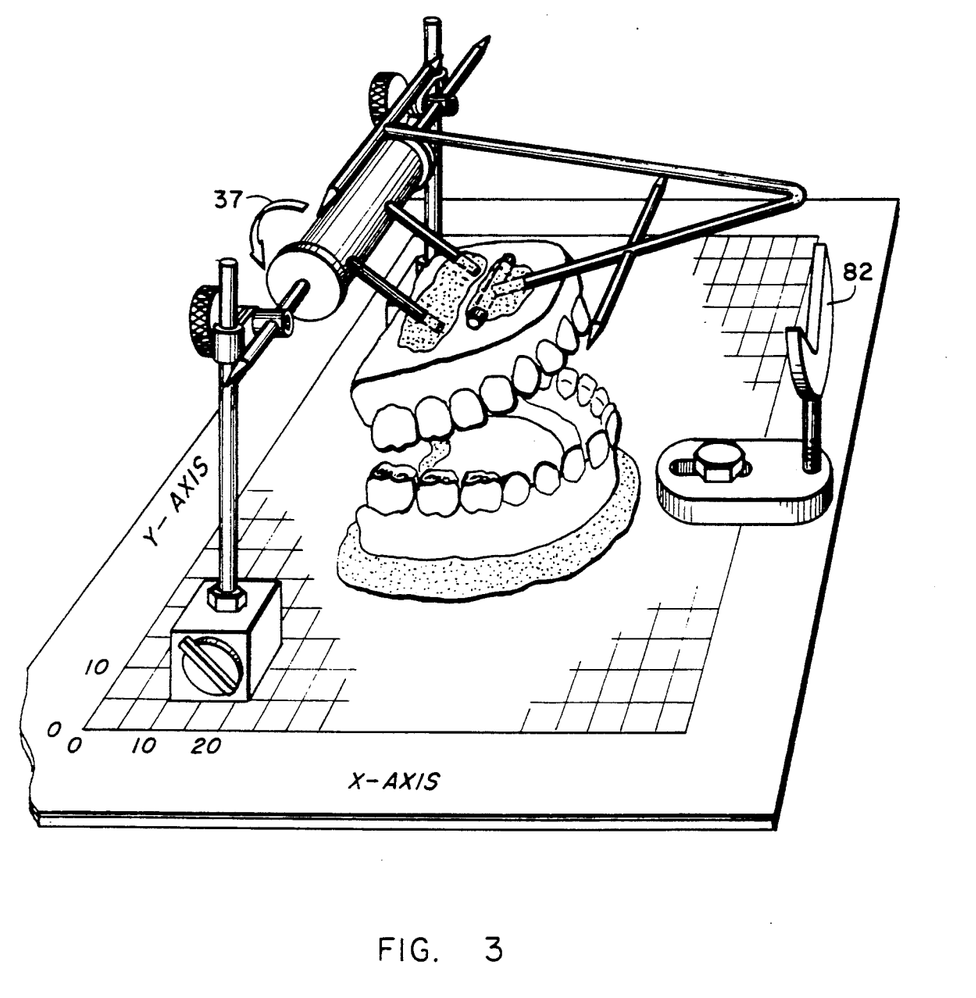
FIG. 3 shows the articulator once it is set up.

Once set up, several tests can be performed with jaw models 46 and 58. With bushings 30 at the inner set of shaft grooves 36 (see FIG. 4) and both wax impressions 70 and 72 removed (as shown in FIG. 3), jaw models 46 and 58 are free to come together. Bringing the jaw models together will indicate the extent of contact between the two. Thus, one can readily identify any high spots that may be preventing some teeth from making solid contact with each other.

A second test is carried out by moving bushings 30 further apart to the outer shaft grooves 38 (see FIG. 5). This allows lateral movement 40 of upper jaw model 46. A V-guide 82 (FIG. 3) is positioned against pointer 48 to limit the lateral movement 40 of upper jaw model 46 for a given opening of the jaws. In this way, the relative movement of the jaws emulates a chewing action. This second test is important in identifying lateral interference that, if left uncorrected, could lead to breakage of an interfering cusp.

A third test is carried out by separating bushings 30 as far as possible, disengaging bushings 30 from cylinder 28 (see FIG. 6). With upper jaw 46 unrestrained (within the limits of the clearance between the ⅞" diameter shaft 24 and the ⅞" inside diameter of cylinder 28) upper jaw 46 is free to settle into maximum engagement with lower jaw 58. This full engagement represents what occurs in a patient's mouth upon closing the actual anatomical jaws tightly together. Such action can shift the relative position of the jaws beyond the natural path along which the condyle joints tend to hold the lower jaw. Forcing teeth together can cause the joints to give. This leads to joint strain which often presents itself while chewing as an annoying "popping" sound from the joint. Joint strain is identified by the articulator as a shift in collinear alignment between the outside diameter of bushings 30 and the inside diameter of cylinder 28.

Principle

The relative movement of human jaws can be closely approximated by a rotational movement about two joints. These two joints define a line about which one jaw rotates with respect to the other.

Figure 7:
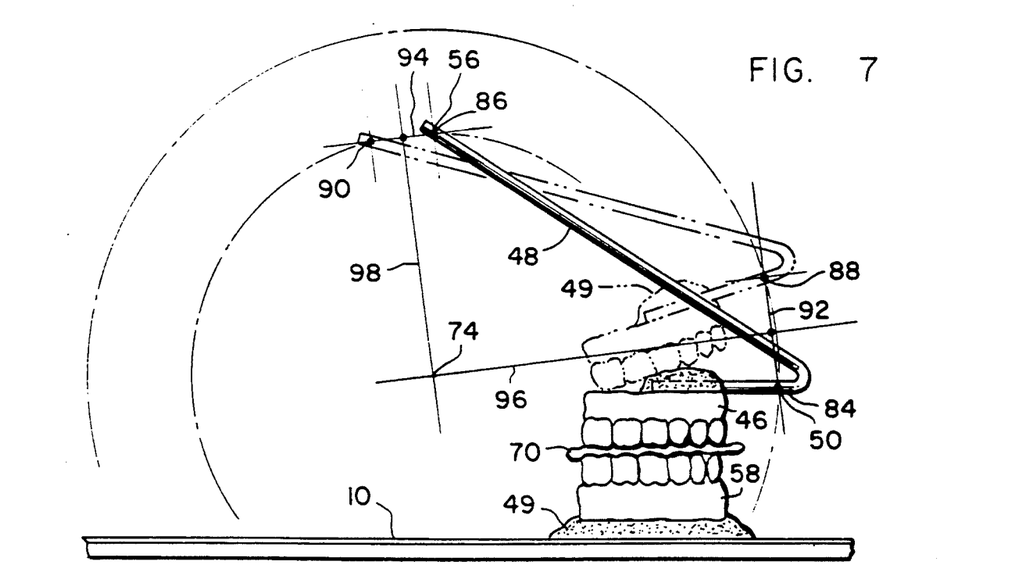
FIG. 7 demonstrates the theory of determining a rotational axis based upon moving the upper jaw model from a first position (solid lines) set by the thinnest wax impression to a second position (phantom lines) set by the thickest wax impression (not shown) sandwiched between the upper and lower jaw models.

Determining the location of two rotational points that define the rotational axis is best understood with reference to a theoretical two-dimensional model (see FIG. 7). With lower jaw 58 fixed, upper jaw 46 and pointer 48 attached to it revolve about an unknown rotational point 74 whose location is to be determined. The location of points 84 and 86 are measured with the thinnest wax impression 70 in place. Points 88 and 90 are found using the thicker wax impression 72. (Note: The thicker wax impression 72 would not actually open the jaws to the extent shown in FIG. 7. The degree of opening shown in FIG. 7 has been exaggerated to more clearly demonstrate the basic principle of operation. The thicker wax impression 72 is not shown in FIG. 7 for clarity.) Chord 92 connects points 84 and 88. Chord 94 connects points 86 and 90. Line 96 intersects the midpoint of chord 92 and is also perpendicular to it. Line 98 intersects the midpoint of chord 94 and is perpendicular to chord 94. The intersection of lines 96 and 98 is the rotational point 74. The second rotational point 76 is found using reference points 52 and 54. The two rotational points 74 and 76 define the rotational axis 78.

It should be apparent that there are a number of other mathematical ways of determining a rotational center point upon taking a plurality of point measurements which are well within the scope of the invention. For example, a third wax impression of intermediate thickness could be used whereby three position measurements could be taken of a single reference point. It is well known that three points define a circle whose center is readily calculated. Another method would be to take an X, Y, and Z reading of points 50 and 52, and take just a Z reading of point 54. The remaining coordinates can be derived knowing the geometry of pointer 48. Of course, a second set of similar readings would need to be taken once jaw model 46 is moved to the second position upon inserting the thicker wax impression 72.

In one embodiment of the invention, lower jaw model 58 is stationary while upper jaw model 46 is moveable. However, it's well within the scope of the invention to have either jaw model moveable.

Adjustable shaft support 18 includes any means for supporting shaft 24. Some examples include, but are not limited to, a magnetic base similar to those widely used by machinists to hold their dial indicators, or a vertical post threaded to a foot having a slot through which a bolt holds the foot to base 10.

The means for attaching jaw model 46 and pointer 48 include any suitable means including, but not limited to, cement, glue, clamps, or threaded fasteners.

Figure 8:
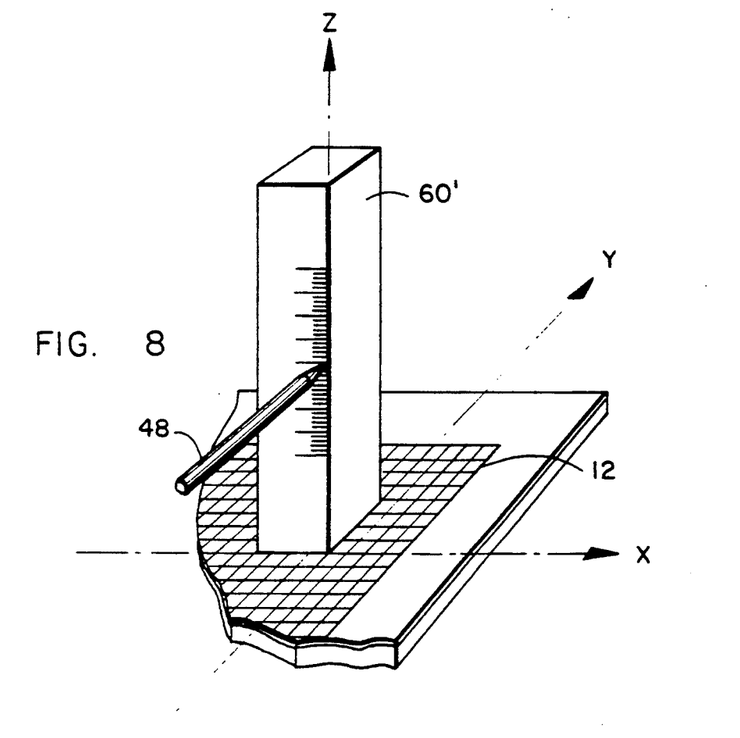
FIG. 8 shows another variation of the rule.

In one embodiment of the invention, the location of the reference points is measured using a height gage 60 having a vertical vernier scale as well as vernier scales on both the X and Y cross-hair axis. However, any other means for measuring the spatial position of the reference points is within the scope of the invention. In another embodiment of the invention, for example, a simple rule 60' (see FIG. 8) approximately $1.5 - \times 1.5'' \times 10''$ high measures the position of the reference points. The lower corner of rule 60' serves as a mark that indicates the X and Y position.

Although, in one embodiment of the invention, V-guide 82 engages pointer 48 to limit the translational movement of upper jaw 46 for a given rotational movement, an equivalent device could be incorporated just about anywhere on the subject invention to serve the same purpose. One such example, well within the scope of the invention, includes a pin (not shown) protruding radially from a shaft (similar to shaft 24) and engaging a triangular opening in a cylinder (similar to cylinder 28).

Although the invention is described with respect to a preferred embodiment, modifications thereto will be apparent to those skilled in the art. Therefore, the scope of the invention is to be determined by reference to the claims which follow:

We claim:

1. A method of determining a rotational axis about which a first jaw model rotates with respect to a datum, comprising the steps of:
   positioning said first jaw model at a first position;
   positioning said first jaw model at a second position;
   taking a plurality of position measurements of said first jaw model at said first and second positions, the value of said position measurements being dependent upon the position of said first jaw model with respect to said datum; and
   calculating the position of said rotational axis as a function of said position measurements.

2. The method as recited in claim 1, wherein each of said position measurements includes an X, Y, and Z component.

3. The method as recited in claim 1, wherein said rotational axis is determined by inputting said position measurements to a computer which calculates X, Y, and Z components of two output points which lie on said rotational axis.

4. The method as recited in claim 1, wherein three position measurements are taken of said first jaw model at said first position and three position measurements are taken of said first jaw model at said second position.

5. The method as recited in claim 1 further comprising the step of positioning a shaft along said rotational axis.

6. The method as recited in claim 5, further comprising the step of disengageably coupling said shaft to said first jaw model to selectively hold and release the axial and radial alignment of said first jaw model with respect to said shaft while allowing rotational movement of said first jaw model about said rotational axis.

7. The method as recited in claim 6, further comprising the step of releasing said axial alignment while maintaining said radial alignment of said first jaw model with respect to said shaft.

8. The method as recited in claim 7, further comprising the step of guiding the movement of said first jaw model with a V-guide.

9. A dental articulator for rotatably mounting a first jaw model relative to a second jaw model, comprising:
   a base;
   a place for attaching said second jaw model to said base;
   a rule adapted to take a plurality of measurements of the position of said first jaw model when said first jaw model is at a first and second position relative to said base; and
   a computer software program for determining a rotational axis of said first jaw model as a function of said measurements.

10. The articulator as recited in claim 9, further comprising graduations associated with said base which in conjunction with graduations on said rule provide X, Y, and Z spatial position coordinates of a measurement taken with said rule.

11. The articulator as recited in claim 9, further comprising a pointer attachable to said first jaw model with at least three reference points from which said rule is adapted to measure.

12. The articulator as recited in claim 9, further comprising an adjustable shaft support adapted to hold a shaft in collinear alignment with said rotational axis.

13. The articulator as recited in claim 12, further comprising a centerline point at each end of said shaft to identify the longitudinal centerline of said shaft.

14. The articulator as recited in claim 12, further comprising a three-position disengageable coupling between said first jaw model and said shaft where in one position of said coupling said first jaw model is free to revolve about said rotational axis but is substantially restricted from moving radially and axially with respect to said shaft, where in another position of said coupling said first jaw model is free to revolve about said rotational axis and slide axially in a direction parallel to said shaft but is substantially restricted from moving radially with respect to said shaft, and where in a third position of said coupling said first jaw model can revolve about said rotational axis and move radially and axially with respect to said shaft.

15. The articulator as recited in claim 9, further comprising a V-guide that limits the axial movement of said first jaw model along said rotational axis for a given rotational movement of said first jaw model about said rotational axis.

16. A dental articulator for rotatably mounting a first jaw model with respect to a second jaw model to emulate the relative movement of two anatomical jaws represented by the models, comprising:
- a base graduated along an X-axis and along a Y-axis;
- a place for attaching said second jaw model to said base;
- a pointer having a plurality of reference points, said pointer being adapted to attach to said first jaw model;
- a rule graduated along a Z-axis and having a mark indicating the X and Y position of said Z-axis when said rule is placed upon said base, with said Z-axis positioned against one reference point of said reference points, said rule identifies an X, Y, and Z spatial position coordinate of said reference point;
- means for calculating two X, Y, and Z output coordinates as a function of a plurality of spatial position coordinates, wherein some of said spatial position coordinates are identified with said first jaw being in a first position and other spacial position coordinates are identified with said first jaw being in a second position;
- a shaft adapted to be coupled to said first jaw, said shaft having two shaft points; and
- an adjustable shaft support adapted to hold said shaft with said two shaft points substantially aligned with said two X, Y, and Z output coordinates.

17. The articulator as recited in claim 16, further comprising a three-position disengageable coupling between said first jaw model and said shaft where in one position of said coupling said first jaw model is free to revolve about said rotational axis but is substantially restricted from moving radially and axially with respect to said shaft, where in another position of said coupling said first jaw model is free to revolve about said rotational axis and slide axially in a direction parallel to said shaft but is substantially restricted from moving radially with respect to said shaft, and where in a third position of said coupling said first jaw model can revolve about said rotational axis and move radially and axially with respect to said shaft.

18. The articulator as recited in claim 16, further comprising a V-guide that limits the axial movement of said first jaw model in a direction parallel to said shaft for a given rotational movement of said first jaw model about the longitudinal center line of said shaft.

* * * * *